(12) United States Patent
Berry et al.

(10) Patent No.: US 7,435,963 B2
(45) Date of Patent: Oct. 14, 2008

(54) FLOW CELL AND METHODS OF USE THEREOF

(75) Inventors: Shaun Berry, Chelmsford, MA (US); Amanda Goyette, Chelmsford, MA (US); Ronald Hoffeld, Cambridge, MA (US); Jonathan Pitts, Westford, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 11/604,881

(22) Filed: Nov. 28, 2006

(65) Prior Publication Data

US 2007/0121114 A1    May 31, 2007

Related U.S. Application Data

(60) Provisional application No. 60/740,246, filed on Nov. 29, 2005.

(51) Int. Cl.
*G01J 5/08* (2006.01)

(52) U.S. Cl. ..................................... 250/343

(58) Field of Classification Search ............... 250/458.1
See application file for complete search history.

(56) References Cited

U.S. PATENT DOCUMENTS

| 5,106,187 | A | * | 4/1992 | Bezanson | ..................... 356/73 |
| 5,861,950 | A | * | 1/1999 | Knowlton | ................... 356/338 |
| 2003/0129090 | A1 | * | 7/2003 | Farrell | ........................ 422/68.1 |
| 2004/0011974 | A1 | * | 1/2004 | Matsuda et al. | ............. 250/574 |

* cited by examiner

*Primary Examiner*—David P. Porta
*Assistant Examiner*—Marcus H Taningco
(74) *Attorney, Agent, or Firm*—Pearl Cohen Zedek Latzer, LLP; Mark S. Cohen

(57) ABSTRACT

This invention provides devices and apparatuses comprising the same, for windowless optical detection of particle-laden samples, for example aerosols or fluid suspensions. The devices make use of passive sheath flow as a mechanism for containing aerosol/fluid suspension flow. The operation of the device reduces particle loss inherent to conventional windowless optical detection schemes. Methods of optical detection and/or analysis of or the particles in a sample using devices of this invention are described.

26 Claims, 2 Drawing Sheets

FLOW CELL AND METHODS OF USE THEREOF

CROSS REFERENCE TO RELATED APPLICATIONS

This Application claims the benefit of U.S. Provisional application Ser. No. 60/740,246, filed Nov. 29, 2005, which is hereby incorporated by reference in its entirety.

BACKGROUND OF THE INVENTION

The invention relates, in some embodiments, to the fields of aerosols and fluidics, windowless optical analysis systems, particle detection systems and particle counter systems, in particular flow cells with passive sheath flow and windowless optical detection.

Optical detection of particles in aerosols and fluid suspensions is essential for a wide range of air and gas quality measurements. It is also utilized in many laboratory analytical techniques. The most straightforward particle detection technique involves passage of the aerosol/suspension through a cylindrical flow cell. Such flow cell may possess but is not limited to two opposing transparent windows in its wall. These parallel windows allow the passage of radiation from an external light source, into and out of the flow cell and into a light detector.

The major drawback of this design is that windows made out of any transparent material (e.g. glass, quartz, $TiO_2$) are subject to particle adhesion. Particles from the aerosol or the suspension adhere to the transparent windows and interfere with light passage through the sample. With time, particles may deposit onto proximal optical surfaces, preventing accurate optical detection of particles and accurate particle counting. To overcome this obstacle, flow cells are sometimes modified to enable "windowless optical detection". Windowless optical detection for fluid suspensions is achieved by having the optical detection system mounted at a small distance away from a nozzle at the end of the flow cell. When the particle suspension is dispensed from the flow cell through the nozzle, the optical detection system probes the particles in the open air.

The major problem with the above-mentioned windowless detection scheme is that once the suspension exits the flow cell, the concentration of the particles changes, and the resulting measurements are inaccurate. Such a scheme also requires complex mechanical design. New methods for accurate windowless detection of particles in aerosols and fluids are required, that will prevent the loss of particles in the open air and that will enable accurate optical detection. New windowless detection methods are required that will allow simplicity of operation.

SUMMARY OF THE INVENTION

In one embodiment, this invention provides a flow cell, comprising:
 a first tube having a first diameter and two diametrically opposed open orifices, wherein said orifices are proximal to a connection point in said tube;
 a second tube coaxial with said first tube, having a second diameter, which is smaller than said first diameter, wherein said second tube is attached to said first tube at said connection point, and said second tube is attached to a sample inlet; and
 a pump operationally connected to said first tube at a point opposite to said connection point whereby application of said pump flows said sample via said inlet, from said second tube to said first tube, and initiates flow diameter expansion and passive sheath flow in said first tube.

In another embodiment, this invention provides a method of particle detection or analysis, the method comprising the steps of:
 a. introducing a sample to a flow cell coupled to an optical detection system, said flow cell comprising:
  i. a first tube having a first diameter and two diametrically opposed open orifices, wherein said orifices are proximal to a connection point in said tube;
  ii. a second tube coaxial with said first tube, having a second diameter, which is smaller than said first diameter, wherein said second tube is attached to said first tube at said connection point, and said second tube is attached to a sample inlet; and
  iii. a pump operationally connected to said first tube at a point opposite to said connection point
 b. applying said pump; and
 c. detecting, analyzing, or a combination thereof a particle in said sample whereby applying said pump flows said sample via said inlet, from said second tube to said first tube, and initiates flow diameter expansion and passive sheath flow in said first tube, which enables detection, analysis or a combination thereof of a particle in said sample.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features, and advantages thereof, may best be understood by reference to the following detailed description when read with the accompanying drawings in which:

DETAILED DESCRIPTION OF THE PRESENT INVENTION

Figure 1:
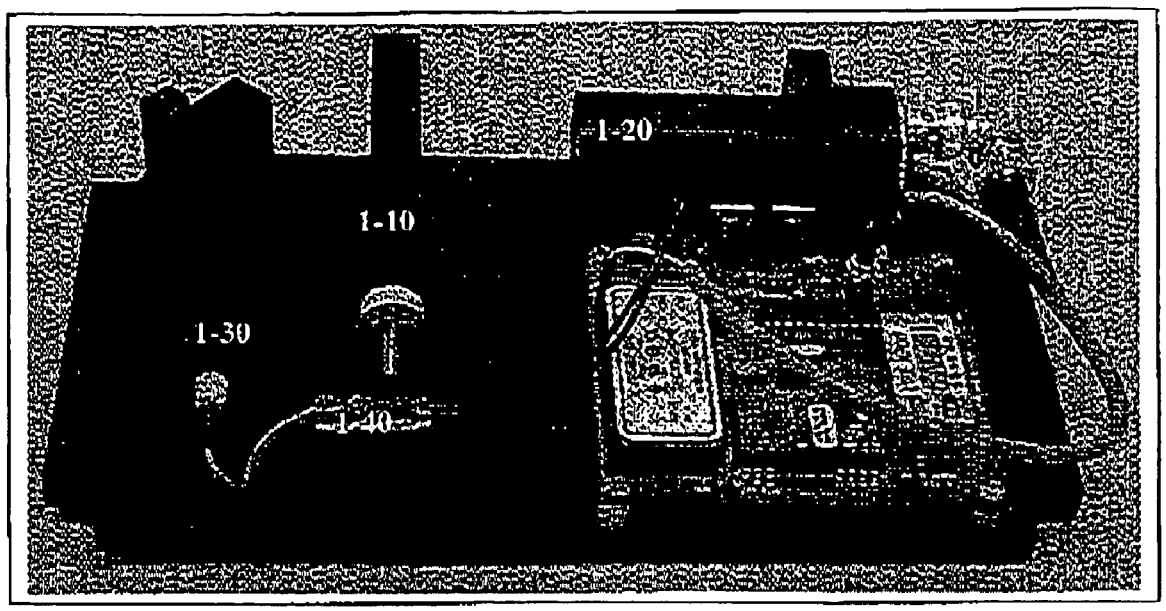
FIG. 1 depicts one embodiment of the flow cell 1-10 and optical detection system. The optical detection system may comprise a light source 1-20, a detector 1-30 and an electronic circuit board 1-40 electronically connected to the light source and the light detector.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

This invention provides, in some embodiments, devices and apparatuses comprising the same, for windowless optical detection of particles in aerosols and fluid suspensions. Such devices utilize passive sheath flow as a mechanism for preventing particle loss during windowless optical detection In one embodiment, this invention provides a flow cell, wherein said flow cell comprises a first tube having a first diameter and two diametrically opposed open orifices, wherein the orifices are proximal to a connection point in said tube; a second tube coaxial with said first tube, having a second diameter, wherein said second diameter is smaller than said first diameter and said second tube is attached to said first tube at said connection point; a pump, wherein said pump is operationally connected to said first tube opposite said connection point, whereby application of said pump flows a particle laden sample into said flow cell from said second tube into said first tube, and initiates flow diameter expansion and passive sheath flow in said first tube.

In one embodiment, the flow cell and other components of the instrument can be made from a wide variety of materials including, but not limited to, glass, silicon dioxide, fused silica, quartz, ceramics, metals and metal alloys, plastics, resins and polymers, etc., or a combination thereof.

In one embodiment, the flow cell comprises a suitable material that prevents adhesion of particles to the flow cell walls.

In another embodiment, the flow cell comprises a material that is functionalized to minimize, reduce or prevent adherence of materials introduced into the device. For example, in one embodiment, the functionalization comprises coating with extracellular matrix protein/s, amino acids, PEG, or PEG functionalized SAM's or is slightly charged to prevent adhesion of cells or cellular material to the surface. In another embodiment, the functionalization may comprise treatment with specific materials to alter flow properties of the material through the device. In another embodiment, such functionalization may be in discrete regions, randomly, or may entirely functionalize an exposed surface of a device of this invention.

In one embodiment, the tubes referred to in the flow cells of this invention may be of any desired geometry, wherein passive sheath flow may be accomplished. In another embodiment, the orifices in the first tube may comprise any geometry as well. In one embodiment, according to this aspect of the invention, the orifices will be of a size to permit ready optical analysis of samples flowed through the flow cell. In one embodiment, the orifices are rectangular in shape, or in another embodiment, approximate a square. In some embodiments, the orifices will have a length of from about 10 micron-2 cm. In some embodiments, the orifices will have a length of roughly 1 cm, or in another embodiment, 500 mm, or in another embodiment, 100 mm. In one embodiment, the orifices will have a width of 1 micron-400 mm. In some embodiments, the orifices will have a width of roughly 10 mm, or in another embodiment, 100 mm.

In one embodiment, the invention provides for a microchip comprising the devices of this invention. In one embodiment, the microchip may be made of a wide variety of materials and can be configured in a large number of ways, as described and exemplified herein, in some embodiments and other embodiments will be apparent to one of skill in the art. The composition of the substrate will depend on a variety of factors, including the techniques used to create the device, the use of the device, the composition of the sample, the material to be assayed, the type of analysis conducted following assay, the size of internal structures, the placement of electronic components, etc. In some embodiments, the devices of the invention will be sterilizable as well, in some embodiments, this is not required.

In some embodiments, the dimensions of the flow cell and of the optical detection system are tailored to specific applications. In one embodiment, the dimensions of the first tube of the flow cell comprise a length of approximately 1 μm-10 mm, and the dimensions of the second tube of the flow cell, in another embodiment, comprise a length of approximately 1.5 μm-20 mm. In some embodiments, the first tube and/or second tube of the flow cell will have a length of approximately 5-400000 μm. In some embodiments, the diameter of the first tube is approximately 10 μm-5 cm. In one embodiment, the diameter of the first tube is approximately 100 μm-2 cm.

In some embodiments, the flow cells comprise inlets and/or outlets, or ports, which are directly connected to a second tube and first tube, respectively. In some embodiments, the ports are formed using conventional tubing, which prevents sample leakage, when fluid is applied to the device, under pressure.

In one embodiment, a "device" or "apparatus" of this invention will comprise at least the elements as described herein. In one embodiment, the devices of this invention comprise at least one flow cell, which may be formed as described herein. In one embodiment, the device may comprise a plurality of flow cells. In one embodiment, the phrase "a plurality of flow cells" refers to more than two, or, in another embodiment, more than 5, or, in other embodiments, more than 10, 50, 100, etc., flow cells. In some embodiments, the flow cells are arrayed in a series, such that multiple measurements can be obtained, upon analysis of the flow-through.

In one embodiment, the devices of this invention comprise a micron size flow cell with micropumps and/or micron size optical fibers as parts of the optical detection system.

In one embodiment, the flow cells of this invention are for use with aerosols or fluid suspensions, comprising particles suspended in air, or liquid, respectively.

In one embodiment, the term "particles" refers to a material which is insoluble in the medium in which it is dispersed. In one embodiment, the particles are in a liquid, or in another in a gas. In one embodiment, the particles comprise a pure substance such as salt, metal, nonmetal inorganic atomic material, nonmetal inorganic molecular material, organic compound or in another embodiment, a homogeneous or a heterogeneous mixture of any combination thereof. In another embodiment, the particles are heterogeneous solid materials. In some embodiments, the particles are cells. In some embodiments, the cells are eukaryotic, and in some embodiments, are suspended in a fluid medium. According to this aspect of the invention, the flow cell may be employed to determine changing size characteristics in a cell population, or in another embodiment, contamination of a medium, or in another embodiment, differentiation of the cells. In another embodiment, the cells analyzed using the flow cells/methods of this invention are prokaryotic, which in some embodiments, represent bacterial contamination of an air supply, in one embodiment, or a water supply, in another embodiment, which may be detected using a device/method of this invention. In some embodiments, the present devices and/or methods provide for superior sensitivity of detection of such contaminants in a given sample.

In some embodiments, the particles are tagged with a detectable marker. In some embodiments, the particles are comprised of a material, which, in another embodiment facilitates their detection via fluorescence or light scattering properties, evaluated or detected by the optical system employed.

In one embodiment, the particles may be present at any concentration and or at any size distribution. In some embodiments, the particles are relatively uniform in size, or in another embodiment, have a relatively polydisperse size distribution, within a sample introduced into the flow cells of this invention, which are then subjected to the methods of this invention.

As will be appreciated by those in the art, virtually any experimental manipulation may have been done on the sample prior to its use in embodiments of the present invention.

In some embodiments, particles in a fluid suspension can also be subjected to an electrical particle detector. The electrical detector comprises a center electrode that can be cylindrical, pear-shaped, elliptical, arrow-shaped, etc. This electrode may be positioned inside the flow cell. A second electrode will be part of or attached to the flow cell wall. External circuitry can be used to control electrical functions. External circuitry can be used to fix the voltage/potential of the center electrodes. In some embodiments, the total charge on the center electrodes can also be controlled. Charge can be controlled relative to the outer electrodes in magnitude, frequency, and phase lag, as above. In some embodiments, electrical and optical detection may be concurrently employed, which, in some embodiments, provides for multiple concurrent analysis, such as, for example, particle size and/or composition. In another embodiment, utilization of both means of analysis provides greater sensitivity in terms of the results thereby obtained. It will be appreciated by one skilled in the art, that any means of analysis wherein optical detection may be utilized as part of sample particle analysis may be accomplished using the devices and/or methods of this invention.

In some embodiments, the sample comprises particles entrained in a gas, or in some embodiments, the particles are entrained in a liquid.

In one embodiment, the flow cell and optical detection system are fabricated on a microchip. In some embodiments, the driving and control electronics and optics can be manufactured on-chip. The driving and control electronics and optics can be a separate electronics/optics module, in some embodiments, an external stand-alone unit or microfabricated electronics/optics. The microfabricated electronics/optics module, in some embodiments, can be wire-bonded to the chip containing the flow cell or can be flip-chip bonded.

In one embodiment, laser-induced forward-scattering, side-scattering and back-scattering of a signal is detected, according to the methods and in use with the devices of this invention. In some embodiments detection is achieved through light diffraction, light reflectance, light refraction or combination thereof, as known in the art. In some embodiments, the light source may be a UV, visible, or IR light source, or generate light of any desired wavelength or combination of wavelengths. Detection of the reflected or scattered light, or emitted light, can be accomplished using various detectors, filters, etc., as is known in the art.

In one embodiment, light is directed to an orifice of the flow cell, and is used to probe a sample within the device. In one embodiment, particles in the sample fluoresce upon exposure to the light source, emission is detected by the detectors. In another embodiment, particles in the device scatter the light, and in some embodiments, multiple detectors collect forward, back and side scattered light.

In one embodiment, the light source may comprise a laser light source, such as, in some embodiments, a laser diode, or in other embodiments, a violet or a red laser diode. In other embodiments, VCSELs, VECSELs, or diode-pumped solid state lasers may be similarly used. In some embodiments, a Brewster's angle laser induced fluorescence detector may used. In some embodiments, one or more beam steering mirrors may be used to direct the beam to a desired location for detection.

EXAMPLES

Example 1

Device Comprising a Particle Counter for Monitoring Air Quality

It is possible to count particles of various sizes using windowless optical detection. One embodiment of such a method utilizes the set up depicted in FIG. 1, wherein a flow cell 1-10 is used. In proximity to the flow cell is an optical detection system comprising a light source 1-20, and a detector 1-30 oriented to facilitate optical analysis. An electronic circuit board 1-40 electronically connected to the light source may be used, with the light detector controlling optical measurement of a given sample, in this embodiment.

The device may comprise an inlet port for the introduction of the air sample into the flow cell. The device will, in another embodiment, comprise a pump connected to an outlet port of the flow cell. The pump draws the sample, for example, a sample of particle-laden air, into the flow cell.

Figure 2:
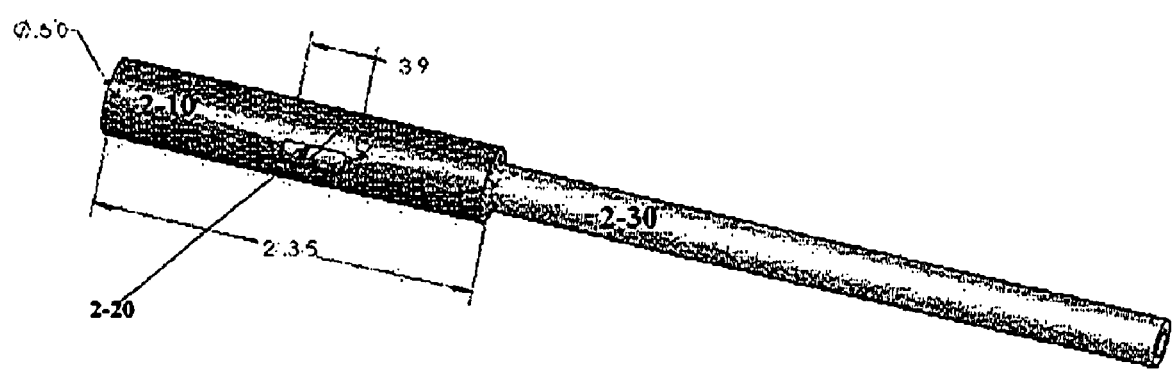
FIG. 2 schematically depicts one embodiment of the flow cell in FIG. 1 (1-10), comprising a first tube 2-10 with two diametrically opposed open orifices 2-20, and a second tube 2-30 coaxial in position with respect to the first tube.

With reference to FIG. 2, the flow cell in some embodiments, comprises two tubes, for example 2-10 and 2-30, as depicted in the figure. The air sample, according to this embodiment, enters the flow cell through the smaller tube 2-30 and passes through the larger tube 2-10. A stream of air concurrently enters the first tube through the orifices positioned proximal to the connection point, at opposite sides of the tube. While both flows are in place, the sample may be analyzed via the use of the mounted optical system. The optical signal generated may be converted to an electrical signal. Analysis may involve comparing the electrical signal of the sample with that of a standard, and for example, particle number may be determined. The dimensions of the flow cell, in one embodiment, may be as follows: the diameter of tube 2-10 may be 5.97 cm, and its length may be 12.7 cm. The diameter of tube 2-30 may be 8.47 cm, and its length may be 11.94 cm.

Example 2

Quantitative Analysis of Metal Ions in Solution

It will be appreciated by one skilled in the art that the device described in Example 1 may be useful in a wide array of applications. In one application, for example analysis of metal ions in solution, the solution containing an unknown concentration of metal ions is reacted with a known concentration of a non-metal anion to form a solid salt. The solution is then evaporated using a heating source, and the vapor comprising the small salt particles is introduced into the flow cell inlet. The optical signal obtained using the flow cell windowless detection system, when the sample is introduced, is compared with the signal of a sample with a known metal ion concentration. Passive sheath flow of clean air through the orifices of the flow cell around the optical detection point prevents particle loss and enables high accuracy measurement.

What is claimed is:

1. A windowless flow cell comprising:
   a) a first tube having a first diameter and two diametrically opposed open orifices, wherein said orifices are proximal to a connection point in said tube;
   b) a second tube coaxial with said first tube, having a second diameter, which is smaller than said first diameter, wherein said second tube is attached to said first tube at said connection point, and said second tube is attached to a sample inlet; and
   c) a pump operationally connected to said first tube at a point opposite to said connection point whereby application of said pump flows said sample via said inlet, from said second tube to said first tube, and initiates flow diameter expansion and passive sheath flow in said first tube and wherein passive sheath flow prevents particle loss from said windowless flow cell.

2. The flow cell of claim 1, wherein said flow cell is operationally connected to an optical detection system.

3. The flow cell of claim 2, wherein said optical detection system comprises a light source and a detector.

4. The flow cell of claim 3, wherein said light source and detector are positioned at a region proximal to said orifices, perpendicularly oriented with respect to the long axis of said first tube.

5. The flow cell of claim 3, wherein said light source is comprised of a laser.

6. The flow cell of claim 3, wherein said light source is comprised of a noncoherent light source.

7. The flow cell of claim 3, wherein said detector detects scattered light.

8. The flow cell of claim 3, wherein said detector detects fluorescence emissions.

9. A windowless flow cell comprising:
a) a first tube having a first diameter and two diametrically opposed open orifices, wherein said orifices are proximal to a connection point in said tube;

b) a second tube coaxial with said first tube, having a second diameter, which is smaller than said first diameter, wherein said second tube is attached to said first tube at said connection point, and said second tube is attached to a sample inlet; and c) a pump operationally connected to said first tube at a point opposite to said connection point whereby application of said pump flows said sample via said inlet, from said second tube to said first tube, and initiates flow diameter expansion and passive sheath flow in said first tube; and wherein said sample is an aerosol.

10. The flow cell of claim 9, wherein said sample comprises particles entrained in a gas.

11. The flow cell of claim 1, wherein said sample comprises particles entrained in a liquid.

12. The flow cell of claim 1, wherein said first tube, said second tube, or a combination thereof has a length, which ranges from 0.5 mm -50 cm.

13. The flow cell of claim 1, wherein said diameter of said first tube ranges from 1-100 mm.

14. The flow cell of claim 1, wherein said diameter of said second tube ranges from 0.5 mm -50 mm.

15. A method of particle detection or analysis comprising the steps of:
a) introducing a sample to a windowless flow cell coupled to an optical detection system, said flow cell comprising:
i) a first tube having a first diameter and two diametrically opposed open orifices, wherein said orifices are proximal to a connection point in said tube;

ii) a second tube coaxial with said first tube, having a second diameter, which is smaller than said first diameter, wherein said second tube is attached to said first tube at said connection point, and said second tube is attached to a sample inlet; and iii) a pump operationally connected to said first tube at a point opposite to said connection point b) applying said pump; and c) detecting, analyzing, or a combination thereof a particle is said sample whereby applying said pump flows said sample via said inlet, from said second tube to said first tube, and initiates flow diameter expansion and passive sheath flow in said first tube, and wherein passive sheath flow prevents particle loss from said windowless flow cell, which enables detection, analysis or a combination thereof of a particle in said sample.

16. The method of claim 15, wherein said optical detection system comprises a light source and a detector.

17. The method of claim 16, wherein said light source and detector are positioned at a region proximal to said orifices, perpendicularly oriented with respect to the long axis of said first tube.

18. The method of claim 16, wherein said light source is comprised of a laser.

19. The method of claim 16, wherein said light source is comprised of a noncoherent light source.

20. The method of claim 16, wherein said detector detects scattered light.

21. The method of claim 16, wherein said detector detects fluorescence emissions.

22. A method of particle detection or analysis comprising the steps of:

a) introducing a sample to a windowless flow cell coupled to an optical detection system, said flow cell comprising:

i) a first tube having a first diameter and two diametrically opposed open orifices, wherein said orifices are proximal to a connection point in said tube;

ii) a second tube coaxial with said first tube, having a second diameter, which is smaller than said first diameter, wherein said second tube is attached to said first tube at said connection point, and said second tube is attached a sample inlet; and iii) a pump operationally connected to said first tube at a point opposite to said connection point b) applying said pump; and c) detecting, analyzing, or a combination thereof a particle in said sample whereby applying said pump flows said sample via said inlet, from said second tube to said first tube, and initiates flow diameter expansion and passive sheath flow in said first tube, which enables detection, analysis or a combination thereof of a particle in said sample; and wherein said sample is a gas.

23. The method of claim 22, wherein said sample comprises particles.

24. The method of claim 15, wherein said sample is liquid.

25. The method of claim 24, wherein said sample comprises particles.

26. The method of claim 23, wherein said sheath flow prevents particle loss.

* * * * *